United States Patent [19]

Barr et al.

[11] Patent Number: 5,380,707
[45] Date of Patent: Jan. 10, 1995

[54] ENHANCED EFFICACY, LONG-LASTING FRAGRANCE COMPOSITION, AND DEODORANT COMPOSITION, FOR MASKING MALODOR, CONTAINING THE FRAGRANCE COMPOSITION

[75] Inventors: Morton L. Barr, East Brunswick; Paul J. Vincenti, Jefferson; Robert V. Burke, Ridgewood, all of N.J.

[73] Assignee: The Mennen Company, Morristown, N.J.

[21] Appl. No.: 105,639

[22] Filed: Aug. 13, 1993

[51] Int. Cl.⁶ .............................................. A61K 1/46
[52] U.S. Cl. .................................... 512/17; 424/76.4; 424/65
[58] Field of Search ................ 512/17; 424/76.4, 65

[56] References Cited

U.S. PATENT DOCUMENTS

| | | | |
|---|---|---|---|
| 4,304,679 | 12/1981 | Hooper et al. | 252/106 |
| 4,322,308 | 3/1982 | Hooper et al. | 252/107 |
| 4,324,703 | 4/1982 | Seldner | 512/11 |
| 4,849,400 | 7/1989 | King | 512/2 |
| 5,198,218 | 3/1993 | Kuznitz et al. | 424/401 |

FOREIGN PATENT DOCUMENTS

WO91/07165 11/1989 WIPO.

OTHER PUBLICATIONS

Keiser, et al "Proceedings of the 1976 International Controlled Releases Pesticide Symposium", Abstract.
Gressel, et al "Safety Evaluation of Four Bicyclic Musk Fragrance . . . " 1980/N. Holland Biomedical Press . . . , pp. 53-58.
Muller, et al "Understanding Fragrance. Origin, History . . . ", The H&R Book of Perfume, p. 67.
Gras "The Overdose", vol. 15, Nov./Dec. 1990, Perfumer & Flavorist.
Gras "The Overdose II", vol. 17, Jan./Feb. 1992, Perfumer.
"Tonalid", Hercules, Apr. 1991, (Aroma Chemicals Specification) Ref. No. 263400.
"Tonalid 2",Hercules, Apr. 1991, (Aroma Chemicals Specification) Ref. No. 263406.
"Tetralide", Bush Boake Allen Product Data, CAS Registry No. 21145-77-7.
"Tonalid" Polak's Frutal Works.
"Tetralide 2", Bush Boake Allen Product Data.

*Primary Examiner*—James H. Reamer
*Attorney, Agent, or Firm*—Antonelli, Terry, Stout & Kraus

[57] ABSTRACT

Disclosed is a fragrance composition having enhanced efficacy for masking malodor for extended periods of time, to be used in deodorant compositions. The fragrance composition includes materials providing fruity, aldehydic and green notes, in an olfactory effective amount, and also includes at least 10% (e.g., 10%-28%) by weight, of the total weight of the fragrance composition, of acetyl hexamethyl tetralin. The fragrance composition can be incorporated in a body deodorant (for example, a deodorant for axillary regions, such as a deodorant stick) to mask body malodor arising in, e.g., axillary regions.

47 Claims, 2 Drawing Sheets

ENHANCED EFFICACY, LONG-LASTING FRAGRANCE COMPOSITION, AND DEODORANT COMPOSITION, FOR MASKING MALODOR, CONTAINING THE FRAGRANCE COMPOSITION

BACKGROUND OF THE INVENTION

The present invention relates to fragrance compositions that are longer lasting and have enhanced efficacy; and deodorant compositions, particularly for treating body malodor (for example, malodor arising in axillary regions of the human body), containing such fragrance compositions. In particular, the present invention is directed to fragrance compositions, and deodorant compositions containing such fragrance compositions, having enhanced efficacy, and retaining, for example, the fragrance of the top note of the fragrance compositions such that the fragrance compositions maintain a relatively balanced fragrance (desired bouquet) for longer periods of time.

Fragrance compositions (such as perfumes) have been used as odor maskants since ancient times, and it is conventional to incorporate fragrance compositions in body deodorants (for example, deodorants to be applied to axillary regions of the human body) in order to overcome body malodor. These fragrance compositions have been incorporated into deodorants together with other deodorant active materials, such as, for example, bacteriostats (e.g., Triclosan).

However, in incorporating fragrance compositions in, for example, deodorants, a problem arises in that the deodorant composition does not sufficiently retain its desired fragrance (aroma) for a sufficient period of time (for example, for 24 hours) after application of the deodorant to the body.

Fragrance formulation is an art in which the senses of the skilled perfumer are more important than chemical analysis. A fragrance results from a variety of components (materials) in a fragrance composition. Ordinarily, fragrances are created by blending materials (ingredients) comprising odoriferous essential oils, extracts from woods, gums, flowers and other botanicals, resins, animal secretions, and synthetic aromatic materials. These materials are blended in order to achieve what are known as "top note" "middle note" and "bottom note" components. The first is the refreshing quality sensed upon application. The last is the essence of the fragrance which stays with the wearer for a long time. The middle note is the perceived quality that bridges from top to bottom note.

The materials themselves are each classified with respect to the aromas (odor) given off, as to providing a green note, floral note, aldehydic note, fruity note, chypre note, oriental note, leather note, tobacco note, fougére note, etc.

In the creation of fragrances, certain materials have generally been selected for their use as fragrance fixatives. These fragrance fixatives are substances which amplify the intensity and lasting qualities of odorous substances of a fragrance. A fragrance fixative has principal activity with respect to the lasting quality and the bottom note of the fragrance.

Various materials are available to the perfumer as fixatives, and include the following:
1. Floral and botanical absolutes, concretes and resinoids;
2. Animal secretions and extracts;
3. Macrocyclic musks;
4. Polycyclic musks; and
5. Nitromusks.

It is well known that fragrance fixatives can distort the nature or character of the fragrance being fixed. Various attempts have been made to fix the fragrance, while avoiding distortion of the nature or character of the fragrance.

One patent addressing this problem is U.S. Pat. No. 4,324,703 to Seldner. This patent incorporates certain methyl glucoside polyols, including alkoxylated methyl glucoside and particularly ethoxylated and propoxylated methyl glucoside, which are essentially odorless, as fragrance fixatives in fragrance compositions. This patent discloses that the described fixatives can be incorporated in various fragrance compositions such as perfumes, colognes, after-bath splashes, after-shaves, perfumed powders, soaps, creams, lotions and virtually every other system which can be fragranced. The contents of this U.S. Pat. No. 4,324,703 to Seldner is incorporated herein by reference in their entirety.

A disadvantage of the fragrance composition of Seldner is that it requires an additional component in the composition.

U.S. Pat. No. 5,120,709 to Cella, et al discloses another technique for providing fixatives for fragrance compositions; and, in particular, provides a technique for enhancing the quality of applied fragrances. This patent discloses that a fixative agent is co-applied with a fragrance form; and that, in a preferred technique, the fixative is independently applied to the same area as the fragrance form. As a specific embodiment, this patent discloses that the fixative agent is applied by overspraying a composition, including the fixative, in a volatile solvent, to the area in which the fragrance form has already been applied. This patent discloses that the fixative agent can be selected from either natural or synthetic fixative agents, and can be a nitromusk, or a macrocyclic, hydroaromatic polycyclic, or oxahydroaromatic compound or a combination thereof. Preferred fixative agents include galaxolide, ethylene brassylate, 4-acetyl-6-t-butyl-1,1-dimethylindane, 11-oxahexadecanolide, musk ambrette musk ketone, musk xylol, civetone or androstene-one or a combination thereof. This patent discloses that the addition of fixative enhances the fragrance form so as to provide a richer and fuller aroma, perceived as being more expensive and finer by the user.

The technique disclosed in U.S. Pat. No. 5,120,709 is a relatively complex procedure, requiring a number of steps and a plurality of compositions. Such technique is impractical for applying body deodorants, for example.

Furthermore, each of U.S. Pat. No. 4,324,703 and No. 5,120,709 is directed to fragrance compositions providing a fragrance such as cologne, and do not describe that the fragrances can be used to mask malodor, such as body malodor arising from perspiration in axillary regions.

It is known that an overload of fixative in a note is no guarantee of good retention of a scent, because substances can hinder one another in their fragrance diffusion. See J. Mueller, *The H & R Book of Perfume* (Understanding Fragrance. Origin, History, Development, Meaning.) (1984), page 67.

U.S. Pat. No. 3,045,047 to Davidson, et al discloses a class of chemical compounds adapted for use as fixatives and blending agents in the manufacture of perfumes and perfumed products, the compounds being acylpolyalkyl-1,2,3,4-tetrahydronaphthalenes, most of the compounds having a pronounced musk-like odor. This patent discloses that the described compounds are synthesized readily from commercially available, inexpensive raw materials. This patent goes on to state that the 6-acetyl-1,1,4,4-tetramethyl-7-ethyl-1,2,3,4-tetrahydronaphthalene, with two quaternary carbon atoms at positions 1 and 4, has a strong, persistent, musk-like odor. This patent further discloses that the presence of two quaternary carbon atoms in the alicyclic portion of the molecule appears to be necessary for the production of a musk-like odor.

In an article by M. Gras, "The Overdose II" in *Perfumer & Flavorist*, Vol. 17 (January/February 1992), pages 2–12, it was reported at page 4 that "Tonalide" is important in men's colognes (Fahrenheit, Dior 1988) at 11%, and used frequently in women's colognes in combination with other musks (Parfume Sacre, Caron 1990) at 5%; and that, nowadays, "Tonalide" is used in almost all laundry products, at levels, as a percentage of the fragrance, of 23% in the Ariel Ultra detergent (1989), 29% in the fabric softener Snuggle Morning Fresh (1989) and up to 30% in Tide Bleach (P&G 1989) where it is used for its great stability and substantivity.

Notwithstanding all of the foregoing, it is still desired to provide a fragrance composition which is capable of masking, e.g., body malodor with enhanced efficacy, for extended periods of time (for example, for at least 24 hours).

It is desired to provide such fragrance composition as part of a deodorant for the body (for example, for the human body), including as part of a deodorant composition for axillary regions of the body, to overcome (mask) body malodor.

SUMMARY OF THE INVENTION

Accordingly, it is an object of the present invention to provide a fragrance composition, having enhanced efficacy for masking malodor (e.g., body malodor, including malodor arising in human axillary regions) for an extended period of time.

It is a further object of the present invention to provide a fragrance composition which maintains its fragrance, including the fragrance of the top note thereof, over extended periods of time.

It is an additional object of the present invention to provide a method of extending the time period that a fragrance composition is fragrant, maintaining aromas from the top note of the fragrance composition.

It is a further object of the present invention to provide a fragrance composition, to be incorporated in a deodorant composition, which masks body malodor for extended periods of time and with enhanced efficacy.

It is a still further object of the present invention to provide a deodorant composition for personal care products, for overcoming (masking) body malodor (such as malodor arising in the axillary regions of the human body), which deodorant composition includes a fragrance composition having an enhanced effect in masking malodor (e.g., body malodor) over extended periods of time.

It is a still further object of the present invention to provide a deodorant composition that does or does not contain polyethylene imine, for application to, e.g., the human body, the deodorant composition including a fragrance composition that masks body malodor, wherein the fragrance composition in the deodorant composition has enhanced efficacy for masking malodor and is long-lasting.

It is a still further object of the present invention to provide a fragrance composition providing a more substantive fragrance on skin of a human, in, for example, axillary regions of the human body.

The foregoing objects are achieved according to the present invention, by a fragrance composition that includes acetyl hexamethyl tetralin in an amount of at least 10% by weight, of the total weight of the fragrance composition, the fragrance composition also containing materials providing each of fruity, aldehydic and green notes, in olfactory effective amounts. These materials providing each of the fruity, aldehydic and green notes form a combination of fruity, aldehydic and green notes, which can form at least part of the top and middle notes of the fragrance composition.

More particularly, the fragrance composition includes acetyl hexamethyl tetralin in an amount of 10%–35%, e.g., 10%–30% or 10%–28%, by weight, of the total weight of the fragrance composition.

Preferably, the materials providing each of fruity, aldehydic and green notes provide "powerful" ("intense") fruity, aldehydic and green notes By "powerful" or "intense", we mean that the materials provide notes that affect the overall fragrance character at low levels, i.e., at a level of less than 0.5% by weight of the material, to the total weight of the fragrance composition.

The name "acetyl hexamethyl tetralin" is the name designated in the *CTFA International Cosmetic Ingredient Dictionary* (4th Ed. 1991) for the compound having the empirical formula $C_{18}H_{26}O$ and that conforms to the following structural formula:

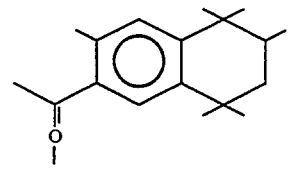

Other names for this compound include 6-acetyl-1,1,2,4,4,7-hexamethyl-1,2,3,4-tetrahydronaphthalene and 1-(5,6,7,8-tetrahydro-3,5,5,6,8,8-hexamethyl-2-naphthalenyl) ethanone. Illustrative names for this compound are "Tonalid", from Hercules, Inc. (Fragrance and Food Ingredients Group), and "Tetralide" from Bush Booke Allen Ltd. (Aroma & Terpene Products). "Tonalid" is an aromatic chemical having a very powerful, warm and radiant musk odor and having a white to off-white solid appearance; this chemical has a melting point of 54° C. minimum, and is very stable in acidic and alkaline media.

Acetyl hexamethyl tetralin is a material known to contribute to bottom notes of fragrance compositions. In the fragrance composition according to the present invention, the acetyl hexamethyl tetralin constitutes part of the bottom note of the fragrance composition, in the specified amount relative to the total fragrance composition. At amounts of acetyl hexamethyl tetralin incorporated in the fragrance composition according to the present invention, the acetyl hexamethyl tetralin primarily acts as a fixative and extender, its impact as an odorant being small. Other materials are necessary to provide desired fragrancing.

The acetyl hexamethyl tetralin primarily maintains the top and middle notes for a longer time. The acetyl hexamethyl tetralin increases the presence of the top and middle notes in the fragrance 24 hours after application, as compared to fragrance compositions containing lesser amounts of acetyl hexamethyl tetralin.

The composition according to the present invention can include other materials contributing to the bottom note, such as galaxolide (1,3,4,6,7,8-hexahydro-4,6,6,7,8,8-hexamethylcyclopenta-gamma-2-benzopyran), hexyl cinnamic aldehyde, etc. Desirably, materials contributing to the bottom note form at least 40% by weight of the total weight of the fragrance composition.

The fragrance composition can also include diluents and/or solvents, such as (but not limited to) benzyl benzoate, diethyl phthalate, dipropylene glycol, etc.

The materials providing the combination of fruity, aldehydic and green notes can be included in the fragrance composition in a relatively large percentage of the top and middle notes, to ensure that some of, e.g., each of these materials (which are relatively volatile) providing these three notes is retained in the composition at least 24 hours after application to the body. This combination, even after 24 hours, gives a lift to the other aromas.

The composition can also include other materials contributing to the top note and the middle note. Fragrance compositions according to the present invention can also include materials providing floral notes, chypre notes, oriental notes, tobacco and leather notes, fougére notes, etc.

By including the acetyl hexamethyl tetralin compound in the fragrance composition containing the materials providing the fruity, aldehydic and green notes, the acetyl hexamethyl tetralin compound being incorporated in an amount of, e.g., 10%–28% by weight, of the total weight of the fragrance composition, the fragrance (aroma) is maintained over extended periods of time; and the fragrance composition can mask malodor (body malodor) with enhanced efficacy, over extended periods of time.

When bottom note compounds such as galaxolide are utilized in relatively large amounts with materials providing the fruity, aldehydic and green notes, enhanced odor masking efficacy over extended periods of time is not achieved. The present invention, utilizing the acetyl hexamethyl tetralin in the specified amounts, in fragrance compositions containing materials providing the fruity, aldehydic and green notes, achieves the objectives of a high efficacy malodor masking, over extended periods of time.

The objectives according to the present invention are also achieved by incorporating the aforementioned fragrance composition in a deodorant composition, for application to, for example, the human body. In this deodorant composition, the fragrance composition acts as a deodorant active material, to mask malodor so as to achieve the deodorant effect. In this aspect of the present invention, the acetyl hexamethyl tetralin is incorporated in the deodorant composition in an amount up to 0.60% by weight of the total weight of the deodorant composition. This deodorant composition can be one that does not contain polyethylene imine.

Various other deodorant active materials, such as bacteriostats, can also be incorporated in the deodorant composition according to the present invention, while still achieving the objectives of the present invention. Thus, the deodorant composition according to the present invention provides enhanced odor masking efficacy over extended periods of time; and can be utilized as a deodorant for axillary regions of the human body, to mask axillary malodor, e.g., arising due to bacterial action on axillary perspiration.

The objectives according to the present invention are further achieved by a method which includes incorporating the above-described amounts of acetyl hexamethyl tetralin in a fragrance composition including materials providing each of fruity, aldehydic and green notes, so as to extend the time period that the fragrance composition is effective, while also providing enhanced odor masking efficacy. Thus, the disclosed method can extend the time period of efficacy of the fragrance composition.

Accordingly, by including the above-described amounts of acetyl hexamethyl tetralin in a fragrance composition together with materials providing fruity, aldehydic and green notes, enhanced efficacy in masking malodor (including body malodor, such as body malodor arising from human axillary regions) can be achieved, with the enhanced efficacy being maintained over extended periods of time. By incorporating the aforementioned fragrance composition in a deodorant composition, for example, for application to the human body, malodors can be masked over extended time periods, and improved substantive fragrances can be provided for personal care formulations.

DETAILED DESCRIPTION OF THE INVENTION

Figure 1:
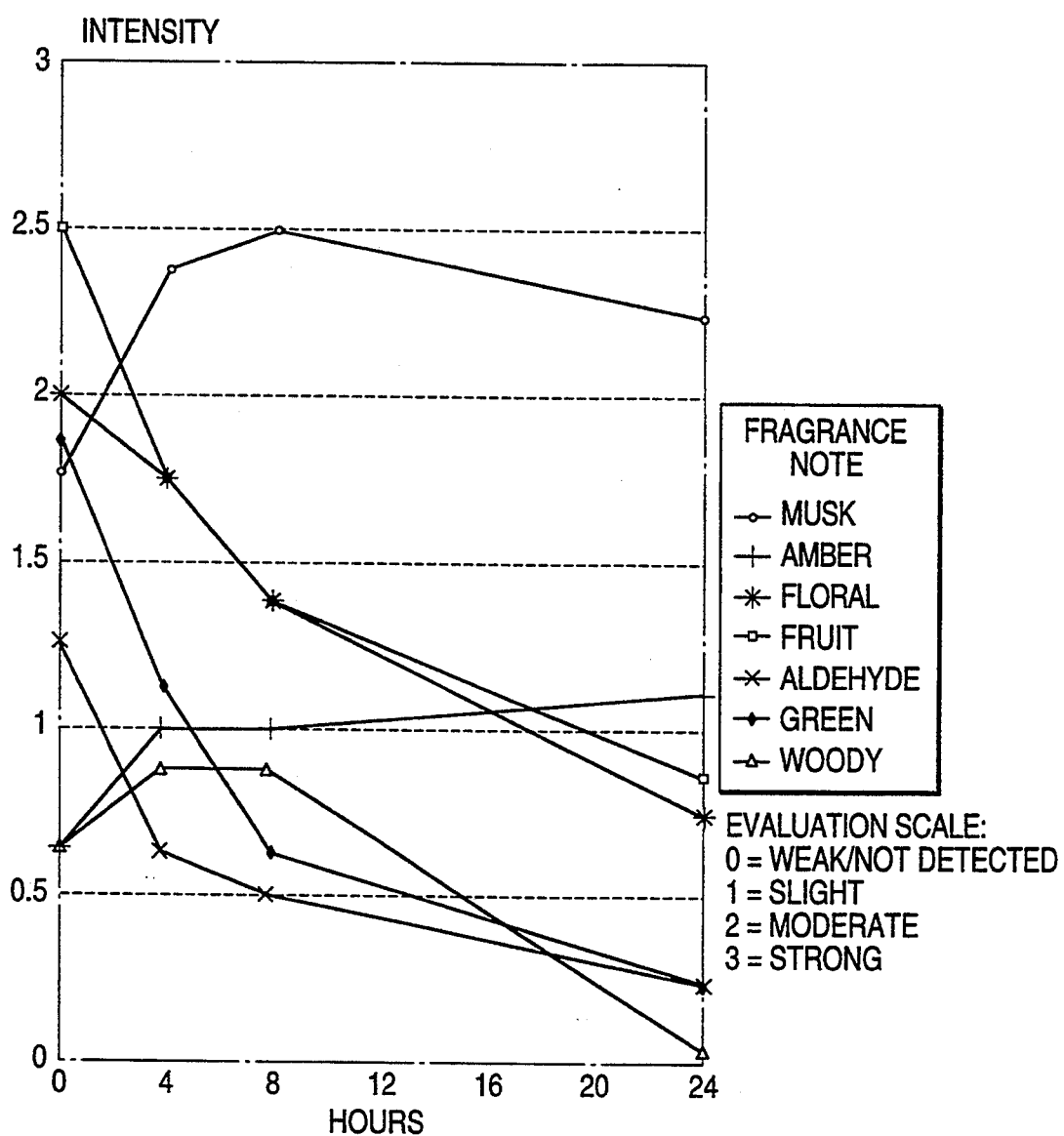
FIG. 1 is a graph showing fragrance intensity as a function of time, for a composition within the scope of the present invention.

While the invention will be described in connection with specific and preferred embodiments, it will be understood that it is not intended to limit the invention to those embodiments. To the contrary, it is intended to cover all alterations, modifications and equivalents as may be included within the spirit and scope of the invention as defined by the appended claims.

Throughout the present disclosure, where compositions are described as including or comprising specific components, it is contemplated that compositions of the present invention also consist essentially of, or consist of, the recited components. Accordingly, throughout the present disclosure any described composition can consist essentially of, or consist of, the recited components.

The present invention contemplates incorporating acetyl hexamethyl tetralin in fragrance compositions also including materials providing each of fruity, aldehydic and green notes. More particularly, e.g., 10%–28% by weight of the fragrance composition is the acetyl hexamethyl tetralin compound. While not limiting, the fragrance composition can include acetyl hexamethyl tetralin in an amount of 10%–25%, or, more specifically, 15%–25%, by weight, of the total weight of the fragrance composition.

The materials providing the green notes utilized in the present invention can include the materials triplal, styralyl acetate and geranyl nitrile. Triplal produces a very intense note, having a low nasal detection threshold and good tenacity. Illustratively, triplal can be included in the fragrance compositions according to the present invention in amounts of 0.05%–3.0% by weight, of the total weight of the fragrance composition.

The styralyl acetate produces a powerful and penetrating green floral, with high impact, even though not as volatile as other greens. It is also called alpha phenylethyl acetate or phenylmethyl carbinyl acetate. The styralyl acetate is, illustratively, included in the fragrance composition in an amount of 0.05% to 3.0% by weight, of the total weight of the fragrance composition.

The geranyl nitrile is penetrating and powerful, being an oily green, and has a lemony-fresh odor with high impact, even though not as volatile as materials providing other green notes. In some respects, the geranyl nitrile is also considered fruity. Another name for the geranyl nitrile is 3,7-dimethyl-2,6-octadiene-1-nitrile (cis and trans isomers). The geranyl nitrile can, illustratively, be included in the fragrance composition in an amount of 0.05%–3.0% by weight, of the total weight of the fragrance composition.

The materials providing fruity notes can include the materials damascone alpha and verdox ester. The damascone alpha is very intense, and is on the border between fruity notes and floral notes. The damascone alpha can, illustratively, be included in the fragrance composition in an amount of 0.1% to 3.0% by weight, of the total weight of the fragrance composition.

The verdox ester is fruity, on the border of fruity and woody, powerful with green undertones. It can be included in the fragrance composition in an amount, by weight, of 0.05% to 3.0%, of the total weight of the fragrance composition.

The materials providing aldehydic notes can include aldehyde C-11 undecylenic. This is also called undecylenic aldehyde or aldehyde C-11, unsaturated. This compound is powerful, with a rosy citrusy aroma having moderate to good tenacity. It can be included in the fragrance composition in an amount of 0.05% to 1.5% by weight, of the total weight of the fragrance composition.

All of the above-listed materials providing green, fruity and aldehydic notes are considered to provide intense (powerful) notes. Generally, the above-listed ingredients have boiling points between 214° C. and 235° C.

Illustratively, a fragrance composition according to the present invention can consist of the above-listed materials providing green, fruity and aldehydic notes, so as to form the top note, for example, with the amounts of the ingredients being in the ranges set forth in the foregoing, together with acetyl hexamethyl tetralin in amounts as discussed previously.

Illustratively, the combined amount of the materials providing green, aldehydic and fruity notes may be 2–15% by weight, of the total weight of the fragrance composition. However, preferably the combined amount of materials producing green, fruity and aldehydic notes is at relatively low levels, for example, 2%–6% by weight, of the total weight of the fragrance composition. Note that these fragrance ingredients can be used in the aggregate at relatively low levels (e.g., 2% by weight), since they are very intense and can be nasally detected at low levels.

The green, fruity and aldehydic components according to the present invention preferably provide intense (or powerful) notes, as such terms are used in Arctander, S., *Perfume & Flavor Chemicals* (1969). Through use of these intense notes, together with the above-described levels of acetyl hexamethyl tetralin, the objectives according to the present invention are achieved. Without the presence of the above-described levels of acetyl hexamethyl tetralin, the intense ingredients cannot provide satisfactory deodorant efficacy (malodor masking) for extended periods of time.

While specific ingredients are set forth in the foregoing as providing the green, fruity and aldehydic notes, the present invention is not limited to these specific ingredients. Other intense, powerful ingredients providing green, fruity and aldehydic notes can be used.

Moreover, the overall fragrance character need not be fruity or green or aldehydic (for example, the overall fragrance character can be woody or floral), as long as ingredients classified as providing the fruity, green and aldehydic notes are included in the composition.

As indicated previously, while essential components of the present invention include materials providing green, fruity and aldehydic notes, together with the acetyl hexamethyl tetralin in the described amounts, the fragrance composition can include other fragrance ingredients (can include materials providing other notes). Thus, the composition can include other materials contributing to the bottom note, in addition to the acetyl hexamethyl tetralin, such as galaxolide, hexyl cinnamic aldehyde, etc. More generally, the fragrance composition can include ingredients providing other notes including floral notes, woody notes, amber notes, other musk notes, etc., so as to provide fragrance compositions having top, middle and bottom notes.

Illustrative fragrance compositions can include specific amounts of ingredients providing various notes, including specific amounts of various ingredients providing the green, fruity and aldehydic notes. Generally, it is desired that the fragrance composition include sufficient amounts of the green, fruity and aldehydic ingredients, such that some of such ingredients remain on the skin 24 hours after application of the composition, e.g., to axillary regions of a human body. By providing a fragrance composition including such amounts of the green, fruity and aldehydic components together with the described amount of acetyl hexamethyl tetralin, the desired masking of malodor is maintained over extended periods of time (e.g., 24 hours).

The present invention also contemplates deodorant compositions incorporating the above-described fragrance composition in a deodorant composition, in a deodorant effective amount. Such deodorant composition can, illustratively, be a composition to be applied to the human body (for example, to axillary regions of the human body). By using the deodorant composition according to the present invention as an axillary deodorant, malodor in the axillary region can be masked for extended periods of time (e.g., at least 24 hours).

The deodorant composition according to the present invention can utilize any conventional vehicle effective for application to the body (e.g., to the human body). For example, the vehicle can be a vehicle for a stick deodorant, an aerosol deodorant, a roll-on, a spray, etc. Such vehicles are well known in the art.

Deodorant compositions incorporating the fragrance composition, according to the present invention, illustratively will contain up to 0.45% by weight of acetyl hexamethyl tetralin, per total weight of the deodorant composition. Desirably, the amount of acetyl hexamethyl tetralin in the deodorant composition is 0.15%–0.45% by weight, of the total weight of the deodorant composition. Through use of such preferred amounts of the tetralin compound in the deodorant composition, together with materials providing the previously described green, fruity and aldehydic notes, as well as any other optional notes, objectives of providing a long-lasting deodorant, that has enhanced efficacy in masking malodor, are achieved.

Other deodorant active agents can be incorporated in the previously described deodorant composition. For example, bacteriostats, illustrated by Triclosan (*CTFA International Cosmetic Ingredient Dictionary* (4th Ed. 1991)), can be incorporated in the deodorant composition to provide even further deodorant protection.

The fragrance composition can be made by mixing the various ingredients to come up with the desired final bouquet or aroma. Generally, the more volatile materials are incorporated near the end of the manufacturing process, to avoid volatilization of ingredients from the composition. At least 10% by weight, and up to (and including), e.g., 28% by weight, of the acetyl hexamethyl tetralin compound, is mixed with ingredients providing at least green, fruity and aldehydic notes, to achieve the objective of a long-lasting fragrance with enhanced efficacy for masking malodor.

The deodorant composition according to the present invention is produced by the same processing steps as prior deodorant compositions have been produced, with the fragrance composition according to the present invention being substituted for previous, conventional fragrance compositions. It is desired that the fragrance composition be added near the end of the deodorant composition manufacture, in order to avoid volatilization of fragrance components, particularly where heating is utilized in forming the deodorant composition (for example, in melting solid ingredients of the vehicle in forming a stick deodorant).

Generally, deodorant compositions according to the present invention are used by, e.g., the consumer in a same manner as done conventionally. For example, with a deodorant composition, including the fragrance composition, of the present invention, in the form of a stick, the stick is elevated out of a dispensing package such that an end of the stick deodorant is exposed, and the stick deodorant is then rubbed on the axillary region of the body so as to leave a thin film of the deodorant composition on the axillary region so as to provide deodorant protection.

It is preferred that the stick product, or any other deodorant composition (such as aerosol, roll-on, etc.) apply at least 0.3 grams of product per 4 inch square, so as to apply an effective amount of the fragrance on the skin.

Fragrance compositions according to the present invention desirably need a sufficient amount of ingredients providing fruity, aldehydic and green notes such that some of these notes remain after 24 hours, so as to achieve objectives of the present invention. Adding intense green, fruity and aldehydic fragrance ingredients even at low levels (e.g., in total, 6% by weight of the total weight of the fragrance composition) improves deodorant clinical efficacy significantly. For example, a deodorant stick formulation containing 1.75% fragrance composition, the fragrance composition being within the scope of the present invention, was found to be a significantly better deodorant than a commercial deodorant stick product containing a similar type and amount of bottom note (long-lasting, substantive) composition, but lacking the intense green, aldehydic and fruity notes. When the deodorant stick formulation as above but not containing the intense green, aldehydic and fruity notes was compared with the commercial deodorant stick product, the commercial deodorant stick product was more effective.

Figure 2:
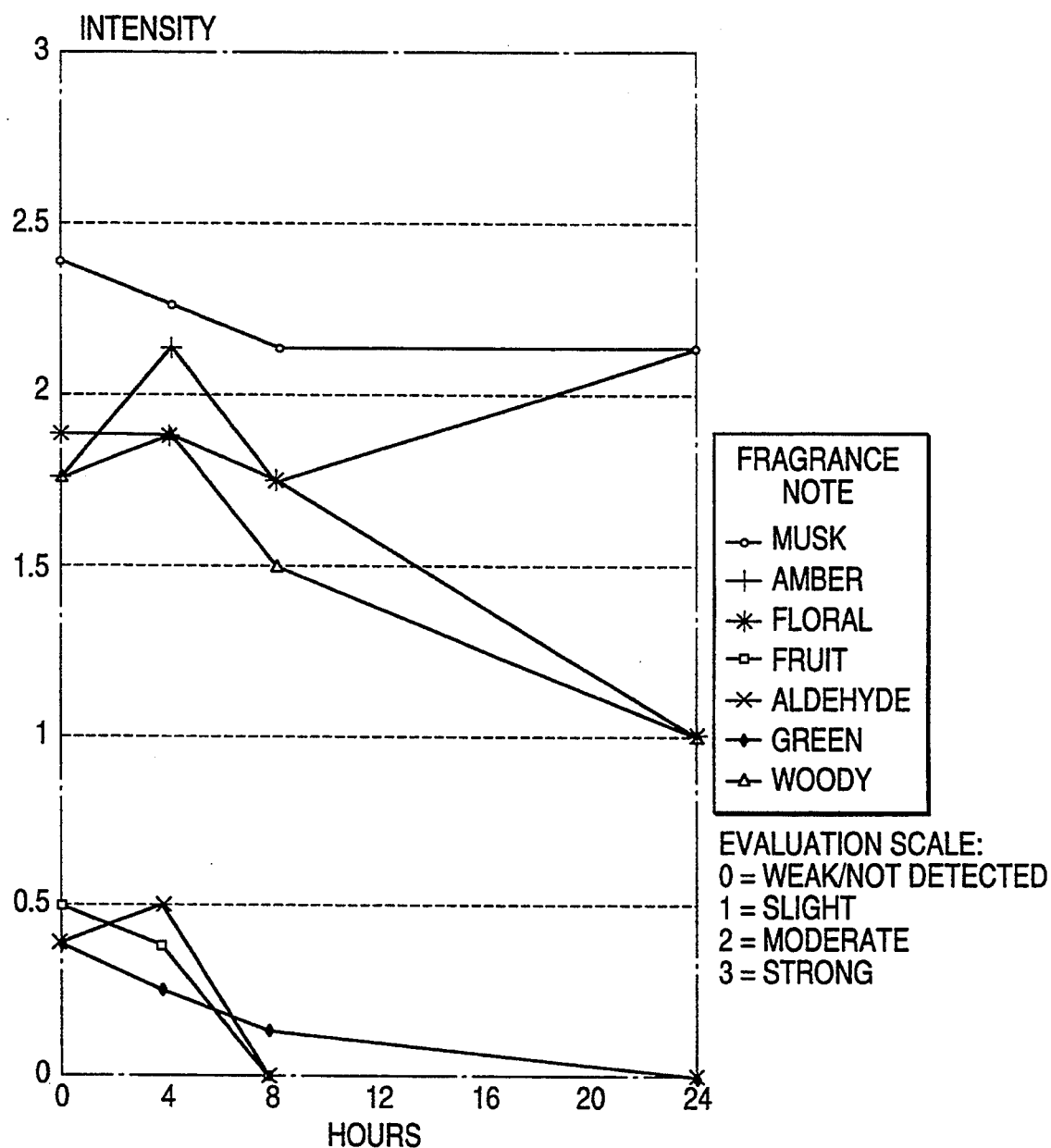
FIG. 2 is a graph showing fragrance intensity as a function of time, for a commercial product that is outside the scope of the present invention.

FIGS. 1 and 2 show notes remaining in the fragrance composition at set times after application of the composition to filter paper, as evaluated by an expert evaluator. As seen in FIG. 1, which represents a composition within the scope of the present invention (but not the present examples), the composition contains sufficient amounts of ingredients providing fruity, aldehydic and green notes, upon application, such that these notes are maintained at detectable levels in the composition even after 24 hours. This composition exhibits significant levels of fruity, aldehydic and green notes immediately after application. On the other hand, FIG. 2 represents a commercial product, wherein amounts of the fruity, aldehydic and green components are sufficiently low at the time of application such that these notes have disappeared by 24 hours after application. The commercial product lacks significant levels of fruity, aldehydic and green notes initially, but more importantly, 24 hours after application of the product to the filter paper. Directly after application of the commercial product, the expert evaluator detected minimal intensity of fruity, aldehydic and green notes; by eight-hours post-application, virtually no such notes were detected. Fruity, aldehydic and green notes were present initially in the commercial product, but were not sufficiently intense and/or in sufficient concentration. This commercial product does not provide the long-lasting malodor masking achieved according to the present invention.

The following Examples further describe and demonstrate embodiments within the scope of the present invention. These Examples are given solely for the purpose of illustration and are not to be construed as limitations of the invention. The first two Examples illustrate the fragrance composition according to the present invention, while the third Example illustrates a deodorant composition (a stick deodorant) according to the present invention. Many variations of these Examples are possible without departing from the spirit and scope of the present invention.

In the following Examples 1 and 2 the amounts are in parts by weight. In the third Example, the amounts are in percent by weight, of the total weight of the composition.

EXAMPLE 1

| | |
|---|---|
| Aldehyde C-11 Undecylenic | 2.00 |
| Ambrox DL (10%) | 110.00 |
| Amyl Cinnamic Aldehyde | 130.00 |
| Cetylia Base | 50.00 |
| Damascenia 185 | 6.00 |
| Damascone Alpha | 8.00 |
| Galaxolide 50 B.B | 466.00 |
| Grisalva | 1.00 |
| Peach Base | 10.00 |
| Sandalwood Oil E.I. | 5.00 |
| Styralyl Acetate | 6.00 |
| "Tonalid" | 200.00 |
| Triplal | 6.00 |
| TOTALS: | 1000.00 |

EXAMPLE 2

| | |
|---|---|
| Aldehyde C-11 Undecylenic | 3.00 |
| Aldehyde C-14 Pure | 1.00 |
| Allyl Amyl Glycolate @10.0% | 1.00 |
| Allyl Caproate | 1.00 |
| Allyl Cyclo Hexyl Propionate | 1.00 |
| Ambrox DL (10%) | 163.00 |
| Amyl Cinnamic Aldehyde | 195.00 |
| Cassis Base 345-B | 1.00 |
| Dimetol | 1.00 |
| Dipropylene Glycol | 150.00 |
| Galaxolide 50 B.B | 150.00 |
| Galbanum Coeur | 1.00 |
| Grisalva | 2.00 |
| Hedione | 6.00 |
| Phenyl Ethyl Alcohol | 95.00 |
| Phenyl Ethyl Iso Butyrate FCC | 1.00 |
| Sandalwood Oil E.I. | 8.00 |
| Styralyl Acetate | 10.00 |
| "Tonalid" | 200.00 |
| Triplal | 9.00 |
| Verdox | 1.00 |
| TOTALS: | 1000.00 |

EXAMPLE 3

| Constituent | Amount |
|---|---|
| Sodium stearate | 7.0% |
| Propylene glycol | 70.0% |
| Water | 20.7% |
| Triclosan | 0.3% |
| Fragrance composition of the present invention | 2.0% |

As seen in Example 3, the fragrance composition according to the present invention can be incorporated in stick deodorants. Illustratively, stick deodorants according to the present invention can include constituents, and amounts, as set forth in the following Table 1.

TABLE 1

| Constituent | Amount | Preferred |
|---|---|---|
| Sodium stearate | 5-8% | 6-7% |
| Propylene glycol | 30-75% | 50-70% |
| Dipropylene glycol | 0-40% | — |
| Water | 5-30% | 15-25% |
| Triclosan | 0-0.5% | 0.2-0.3% |
| Fragrance composition of the present invention | 0.25-2.5% | 1.25-2.0% |

The foregoing Table 1 sets forth illustrative constituents and amounts, including more general and preferred amounts. This Table 1 is illustrative and not limiting of the present invention.

As seen in the foregoing, deodorant compositions according to the present invention include fragrance compositions, with or without other deodorant active materials, such as Triclosan. Thus, according to the deodorant composition of the present invention the fragrance composition acts as an active deodorant agent, e.g., without other active deodorant agents, such as sodium bicarbonate, and without, e.g., polyethylene imine. Various of these other active deodorant agents can be incorporated in deodorant compositions having fragrance compositions according to the present invention.

Accordingly, through the present invention, a deodorant composition which is long-lasting and which has enhanced efficacy in masking malodor, is achieved.

The following U.S. patent application, filed concurrently herewith, the contents of which are incorporated herein by reference in their entirety, contains subject matter related to the subject matter of the present application:

Morton L. Barr, Paul J. Vincenti and Robert V. Burke, "Fragrance Composition Containing Substantial Amounts of Acetyl Hexamethyl Tetralin, and Deodorant Composition Containing the Fragrance Composition" (Attorney Docket No. 851.32240X00 U.S. patent application Ser. No. 08/105,806, filed Aug. 13, 1993).

While we have shown and described several embodiments in accordance with the present invention, it is understood that the same is not limited thereto, but is susceptible to numerous changes and modifications as known to one having ordinary skill in the art, and we therefore do not wish to be limited to the details shown and described herein, but intend to cover all such modifications as are encompassed by the scope of the appended claims.

We claim:

1. A fragrance composition for masking malodor comprising at least materials providing each of fruity notes, aldehydic notes and green notes, and further including 10-28% by weight, of the total weight of the fragrance composition, of acetyl hexamethyl tetralin, the materials being provided in olfactory effective amounts, whereby presence of top and middle notes in the fragrance composition, 24 hours after application of the fragrance composition, is increased, as compared to that of fragrance compositions containing lesser amounts of acetyl hexamethyl tetralin.

2. The fragrance composition according to claim 1, wherein acetyl hexamethyl tetralin is included in the fragrance composition in an amount of 15-25% by weight, of the total weight of the fragrance composition.

3. The fragrance composition according to claim 1, wherein the fragrance composition includes 15%-28% by weight, of the total weight of the fragrance composition, of acetyl hexamethyl tetralin.

4. The fragrance composition according to claim 3, wherein a total amount of the materials providing the fruity notes, aldehydic notes and green notes is 2-15% by weight of the total weight of the fragrance composition.

5. The fragrance composition according to claim 4, wherein said total amount of the materials providing the fruity notes, aldehydic notes and green notes is 2-6% by weight of the total weight of the fragrance composition.

6. The fragrance composition according to claim 4, wherein said materials providing the green notes include at least one of triplal, styralyl acetate and geranyl nitrile; said materials providing the fruity notes include at least one of damascone alpha and verdox ester; and said materials providing the aldehydic notes include aldehyde C-11 undecylenic.

7. The fragrance composition according to claim 4, wherein said materials include triplal, styralyl acetate, geranyl nitrile, damascone alpha, verdox ester, and aldehyde C-11 undecylenic.

8. The fragrance composition according to claim 7, wherein the fragrance composition includes, in amount by weight of the total weight of the composition, 0.05% to 3.0% triplal, 0.05% to 3.0% styralyl acetate, 0.05% to 3.0% geranyl nitrile, 0.1% to 3.0% damascone alpha, 0.05% to 3.0% verdox ester, and 0.05% to 1.5% aldehyde C-11 undecylenic.

9. The fragrance composition according to claim 8, wherein acetyl hexamethyl tetralin is included in the fragrance composition in an amount of 15–25% by weight, of the total weight of the fragrance composition.

10. The fragrance composition according to claim 3, wherein the acetyl hexamethyl tetralin contributes to a bottom note of the fragrance composition, the fragrance composition including further materials contributing to the bottom note, in addition to the acetyl hexamethyl tetralin.

11. The fragrance composition according to claim 10, wherein said further materials contributing to the bottom note, in addition to the acetyl hexamethyl tetralin, are at least one selected from the group consisting of 1,3,4,6,7,8-hexahydro-4,6,6,7,8,8-hexamethyl-cyclopenta-gamma-2-benzopyran and hexyl cinnamic aldehyde.

12. The fragrance composition according to claim 3, wherein the materials providing the fruity notes, aldehydic notes and green notes are present in the fragrance composition in such amount that the fruity notes, aldehydic notes and green notes remain present in applied fragrance composition 24 hours after application of the fragrance composition.

13. The fragrance composition according to claim 3, the composition also including materials providing musk notes, amber notes, floral notes and woody notes.

14. The fragrance composition according to claim 13, wherein the materials providing the fruity notes, the aldehydic notes, the green notes, the musk notes, the amber notes, the floral notes and the woody notes are each included in the fragrance composition in amounts such that each of the fruity notes, the aldehydic notes, the green notes, the musk notes, the amber notes, the floral notes and the woody notes is present in applied fragrance composition 24 hours after application of the fragrance composition.

15. The fragrance composition according to claim 3, wherein the fragrance composition is for application to a human, the malodor being human malodor.

16. The fragrance composition according to claim 15, wherein the fragrance composition is for application to axillary regions of the human, the malodor being axillary malodor.

17. A deodorant composition for application to a body, comprising the fragrance composition of claim 3, in a deodorant effective amount, in a vehicle effective for application to the body.

18. The deodorant composition according to claim 17, said body being a human body.

19. The deodorant composition according to claim 17, wherein the acetyl hexamethyl tetralin is included in the deodorant composition in an amount up to 0.45% by weight of the total weight of the deodorant composition.

20. The deodorant composition according to claim 19, wherein the amount of the acetyl hexamethyl tetralin included in the deodorant composition is 0.15%–0.45% by weight of the total weight of the deodorant composition.

21. The deodorant composition according to claim 20, wherein said vehicle is a vehicle for a stick deodorant composition, the deodorant composition being a solid stick deodorant product.

22. The deodorant composition according to claim 21, wherein said vehicle permits a payout of at least 0.3 gms of the deodorant composition per 4 in$^2$ of the body to which the deodorant composition is applied.

23. The deodorant composition according to claim 22, wherein said body is a human body.

24. The deodorant composition according to claim 22, wherein said body is axillary regions of the human body.

25. A deodorant composition for application to a body, comprising the fragrance composition of claim 4, in a deodorant effective amount, in a vehicle effective for application to the body.

26. The deodorant composition according to claim 25, wherein the amount of the acetyl hexamethyl tetralin included in the deodorant composition is 0.15%–0.45% by weight of the total weight of the deodorant composition.

27. A deodorant composition for application to a body, comprising the fragrance composition of claim 8, in a deodorant effective amount, in a vehicle effective for application to the body.

28. The deodorant composition according to claim 27, wherein the amount of the acetyl hexamethyl tetralin included in the deodorant composition is 0.15%–0.45% by weight of the total weight of the deodorant composition.

29. A deodorant composition for application to a body, comprising the fragrance composition of claim 14, in a deodorant effective amount, in a vehicle effective for application to the body.

30. The deodorant composition according to claim 29, wherein the amount of the acetyl hexamethyl tetralin included in the deodorant composition is 0.15%–0.45% by weight of the total weight of the deodorant composition.

31. A method of extending the time period over which a fragrance composition provides malodor masking, while providing a fragrance composition having enhanced malodor masking efficacy, comprising incorporating acetyl hexamethyl tetralin, in an amount of 10%–28% by weight, of the total weight of the fragrance composition, in a combination including materials providing fruity notes, aldehydic notes and green notes, said combination being in the fragrance composition in an olfactory effective amount, whereby presence of top and middle notes in the fragrance composition, 24 hours after application of the fragrance composition, is increased, as compared to that of fragrance compositions containing lesser amounts of acetyl hexamethyl tetralin.

32. The method according to claim 31, wherein the acetyl hexamethyl tetralin is incorporated in the fragrance composition of 15%–28% by weight, of the total weight of the fragrance composition.

33. The method according to claim 31, wherein the acetyl hexamethyl tetralin is incorporated in the fragrance composition in an amount of 15%–25% weight, of the total weight of the fragrance composition.

34. The method according to claim 32, wherein said materials providing fruity notes, aldehydic notes and green notes comprise triplal, styralyl acetate, geranyl nitrile, damascone alpha, verdox ester and aldehyde C-11 undecylenic.

35. The method according to claim 34, wherein the triplal is included in an amount of 0.05%–3.0% by weight, the styralyl acetate is included in an amount of 0.05%–3.0% by weight, the geranyl nitrile is included in an amount of 0.05%–3.0% by weight, the damascone alpha is included in an amount of 0.1%–3.0% by weight, the verdox ester is included in an amount of 0.05%–3.0% by weight, and the aldehyde C-11 undecylenic is included in an amount of 0.05%–1.5% by weight, of the total weight of the fragrance composition.

36. The method according to claim 32, wherein the materials providing fruity notes, aldehydic notes and green notes are included in the fragrance composition in an amount of 2%–15% the total weight of the fragrance composition.

37. The fragrance composition according to claim 1, wherein the acetyl hexamethyl tetralin is 6-acetyl-1,1,2,4,4,7-hexamethyl-1,2,3,4-tetrahydronaphthalene.

38. The fragrance composition according to claim 37, wherein the fragrance composition includes 15%–28% by weight, of the total weight of the of the fragrance composition, of 6-acetyl-1,1,2,4,4,7-hexamethyl-1,2,3,4-tetrahydronaphthalene.

39. A deodorant composition for application to a body, comprising the fragrance composition of claim 38, in a deodorant effective amount, in a vehicle effective for application to the body.

40. The deodorant composition according to claim 39, wherein the body is a human body.

41. The deodorant composition according to claim 39, including additional deodorant active materials.

42. The deodorant composition according to claim 41, wherein the additional deodorant active materials include bacteriostats.

43. The deodorant composition according to claim 39, consisting essentially of the fragrance composition and the vehicle.

44. The deodorant composition according to claim 17, consisting essentially of the fragrance composition and the vehicle.

45. The method according to claim 31, wherein said acetyl hexamethyl tetralin is 6-acetyl-1,1,2,4,4,7-hexamethyl-1,2,3,4-tetrahydronaphthalene.

46. The method according to claim 45, wherein the 6-acetyl-1,1,2,4,4,7-hexamethyl-1,2,3,4-tetrahydronaphthalene is incorporated in an amount of 15%–28% by weight, of the total weight of the fragrance composition.

47. The method according to claim 46, wherein the materials providing fruity notes, aldehydic notes and green notes are included in the fragrance composition in an amount of 2%–15% of the total weight of the fragrance composition.

* * * * *